United States Patent
Howard et al.

(10) Patent No.: US 7,150,880 B2
(45) Date of Patent: *Dec. 19, 2006

(54) COMPOSITIONS CONTAINING CREATINE AND CREATININE AND A METHYL XANTHINE

(75) Inventors: Alan N. Howard, Great Shelford (GB); Roger C. Harris, Newmarket (GB)

(73) Assignee: The Original Creatine Patent Co. Ltd., Cambridge (GB)

( * ) Notice: Subject to any disclaimer, the term of this patent is extended or adjusted under 35 U.S.C. 154(b) by 441 days.

This patent is subject to a terminal disclaimer.

(21) Appl. No.: 10/368,427

(22) Filed: Feb. 20, 2003

(65) Prior Publication Data

US 2003/0219500 A1   Nov. 27, 2003

Related U.S. Application Data

(63) Continuation-in-part of application No. 09/917,634, filed on Jul. 31, 2001, now Pat. No. 6,524,611, and a continuation-in-part of application No. 09/419,922, filed on Oct. 18, 1999, now Pat. No. 6,274,161, which is a continuation-in-part of application No. 08/866,517, filed on May 30, 1997, now Pat. No. 5,968,544.

(30) Foreign Application Priority Data

May 31, 1996 (GB) ................................. 9611356.8
Mar. 2, 2001 (GB) ................................. 0105205.9

(51) Int. Cl.
    *A61K 9/00* (2006.01)
(52) U.S. Cl. ........................ 424/439; 424/400
(58) Field of Classification Search ................ 423/439; 424/400, 439
See application file for complete search history.

(56) References Cited

U.S. PATENT DOCUMENTS

| | | | |
|---|---|---|---|
| 3,615,600 A | 10/1971 | Tonsbeek | |
| 4,371,521 A | 2/1983 | Izrael | |
| 4,464,409 A | 8/1984 | de Rooij | |
| 4,647,453 A | 3/1987 | Meisner | |
| 4,772,591 A | 9/1988 | Meisner | |
| 5,077,313 A | 12/1991 | Lubec | |
| 5,091,404 A | 2/1992 | Elgebaly | |
| 5,308,627 A | 5/1994 | Umbdenstock, Jr. | |
| 5,332,579 A | 7/1994 | Umbdenstock | |
| 5,391,550 A | 2/1995 | Carniglia et al. | |
| 5,397,786 A | 3/1995 | Simone | |
| 5,507,790 A * | 4/1996 | Weiss ........................ 607/100 |
| 5,541,188 A * | 7/1996 | Maltin ................... 514/263.34 |
| 5,767,159 A | 6/1998 | Hultman et al. | |
| 5,773,473 A | 6/1998 | Green et al. | |
| 5,908,864 A | 6/1999 | Casey | |
| 5,968,544 A | 10/1999 | Howard et al. | |

(Continued)

FOREIGN PATENT DOCUMENTS

EP          0199117 A2     10/1986

(Continued)

*Primary Examiner*—Michael G. Hartley
*Assistant Examiner*—Simon J. Oh
(74) *Attorney, Agent, or Firm*—Perry E. Van Over; Manelli Denison & Selter PLLC

(57) ABSTRACT

A composition for human consumption, comprising creatine and creatinine, the latter being in sufficient quantity to render creatine in an aqueous medium substantially stable, and a methyl xanthine; and a method of making the composition is provided.

41 Claims, 8 Drawing Sheets

U.S. PATENT DOCUMENTS

| | | | |
|---|---|---|---|
| 5,968,900 A * | 10/1999 | Greenhaff et al. | 514/3 |
| 6,075,031 A | 6/2000 | Kaddurah-Daouk et al. | |
| 6,168,802 B1 | 1/2001 | Howard et al. | |
| 6,274,161 B1 | 8/2001 | Howard et al. | |
| 6,524,611 B1 * | 2/2003 | Howard et al. | 424/439 |
| 2001/0008641 A1 | 7/2001 | Krotzer | |

FOREIGN PATENT DOCUMENTS

| | | |
|---|---|---|
| EP | 0222257 A2 | 5/1987 |
| EP | 0449787 A2 | 10/1991 |
| EP | 0 669 083 A2 | 8/1995 |
| EP | 0669083 A2 | 8/1995 |
| GB | 2313544 A | 12/1997 |
| JP | 59025663 | 2/1984 |
| JP | 950087771 | 9/1996 |
| WO | WO94/02127 | 2/1994 |
| WO | WO94/15488 | 7/1994 |
| WO | WO94/17794 | 8/1994 |
| WO | WO96/04240 A1 | 2/1996 |
| WO | WO96/14063 | 5/1996 |
| WO | WO96/36348 | 11/1996 |
| WO | WO97/45026 | 12/1997 |
| WO | WO97/45026 A1 | 12/1997 |
| WO | WO98/53704 | 12/1998 |
| WO | WO00/74500 A1 | 12/2000 |
| WO | WO02/069740 A | 9/2002 |

* cited by examiner

COMPOSITIONS CONTAINING CREATINE AND CREATININE AND A METHYL XANTHINE

This application is a Continuation In Part of U.S. application Ser. No. 09/917,634, filed Jul. 31, 2001 now U.S. Pat. No. 6,524,611, which claims priority to Great Britain Application No. 0105205.9, filed Mar. 2, 2001 and is a Continuation In Part of U.S. application Ser. No. 09/419,922, filed Oct. 18, 1999 (now U.S. Pat. No. 6,274,161), which is a Continuation In Part of U.S. application Ser. No. 08/866,517, filed May 30, 1997 (now U.S. Pat. No. 5,968,544), which claims priority to Great Britain Application No. 9611356.8, filed May 31, 1996. The entirety of all the above applications are incorporated herein by reference.

RELATED ART

Related U.S. application Ser. No. 09/324,119, which issued as U.S. Pat. No. 6,168,802 on Jan. 2, 2001, which is a Continuation In Part of U.S. application Ser. No. 08/866,517 and issued as U.S. Pat. No. 5,968,544 on Oct. 19, 1999 is fully incorporated herein by reference.

FIELD OF THE INVENTION

This invention relates to compositions for human consumption comprising creatine and creatinine and at least one methyl xanthine and to a method of providing such compositions.

BACKGROUND OF THE INVENTION

In the last few years there has been considerable interest among athletes in creatine, which occurs abundantly in skeletal muscle. Creatine plays a pivotal role in the regulation and homeostasis of skeletal muscle energy metabolism and it is now generally accepted that the maintenance of phospho-creatine availability is important to the continuation of muscle force production. Creatine may also be involved in other processes concerned with protein synthesis and hypertrophy of muscle fibers during training. Although creatine synthesis occurs in the liver, kidney and pancreas it has been known for sometime that the oral ingestion of creatine will add to the whole body creatine pool, and it has been shown that the ingestion of 20 to 30 g creatine monohydrate ($Cr.H_2O$) per day for several days can lead to a greater than 20% increase in human skeletal muscle total creatine content. Thus, WO94/02127 discloses the administration of creatine monohydrate in amounts of at least 15 g (or 0.2–0.4 g/kg body weight) per day, for at least 2 days, for increasing muscular strength.

In fact, it was subsequently found that after several days of supplementation (20 g per day) with creatine monohydrate in order to attain initial elevation of the tissue stores, thereafter it takes no more than 2 to 3 g per day to maintain the newly elevated concentration. Supplementation with any bioavailable source of creatine (i.e. creatine supplementation) in an appropriate dose can provide improvements to athletes involved in explosive events, which include all events lasting from a few seconds to a few minutes (such as sprinting, swimming, weight-lifting etc). Endurance performance in events lasting longer than about 30 minutes appear less affected by creatine supplementation except where this involves short periods of increased energy output particularly when the local muscle carbohydrate stores have become depleted. Creatine is a normal food component and is not a drug and its use is not contrary to official regulations. It is possible that the greatest benefits of creatine supplementation are experienced by the elderly, vegetarians or those who eat no meat or fish, since these people tend to have low muscle creatine contents.

The inclusion of creatine in a drink would be highly desirable as a convenient means of providing creatine supplementation.

However, most drinks, especially fruit-flavored drinks, are acidic. It is well known that the creatine molecule is unstable in aqueous solutions at acid or neutral pH, and is converted into the related compound creatinine. This is highly significant as creatinine has no muscle performance-enhancing effect and is excreted from the human body as a waste product in urine. In view of the foregoing, EP 0 669 083 teaches that aqueous drinks for human consumption comprising creatine must be weakly alkaline, in order to limit the conversion of creatine into creatinine, and this has become the generally accepted opinion.

Furthermore, creatine and its derivatives have been used in the past but only for the preparation of products with a meaty or savory flavor. For instance, Tonsbeek (U.S. Pat. No. 3,615,600) discloses and is concerned with artificial flavoring, describing mixtures imparting a meaty flavor to foods. Similarly de Rooji (U.S. Pat. No. 4,464,409) is concerned with meat flavoring. Yamazaki (JP-A-59035663) prepares a meat flavor by heating a mixture comprising creatine at pH 5.0–7.0 at a temperature of 80–130° C. for 30–120 minutes. Under these conditions most of the creatine is converted to creatinine.

The inventors believe that it would not occur to the persons skilled in the art to add creatinine (used hitherto as a meat or savory flavoring agent) to compositions which were intended to have a flavor (especially a fruit flavor) other than meaty or savory. The person skilled in the art might have expected the addition of creatinine to result in an unpalatable combination of fruit and meat flavors, whereas in fact the inventors have found that the resulting combination does not impart an undesirable meaty flavor.

WO 97/45026 discloses an acidic composition for human consumption comprising creatine and its derivatives, the composition being provided as a dry powder or in liquid or semi-liquid form. The compositions disclosed therein are stable at refrigerated temperatures (4° C.) for prolonged periods but stable at ambient temperature for relatively short periods (e.g. up to, but not exceeding, 7 days).

WO 00/74500 discloses compositions comprising creatine and its derivatives suspended in aloe vera gel, which compositions were stable (with respect to the conversion of creatine to creatinine) at room temperature for 2 weeks or more, depending on the initial concentration of creatine in the composition.

Both WO 97/45026 and WO 00/74500 stress the desirability of preventing the conversion of creatine to creatinine, and neither document suggests the deliberate addition of creatinine to a creatine-containing composition intended for human consumption.

A very high proportion of the population consume drinks containing methyl xanthines. The methyl xanthines are a class of chemical compounds which include caffeine, theobromine, and theophylline. These are present in coffee, tea and cocoa. The major methyl xanthine in coffee is caffeine, in tea caffeine and theophylline and in cocoa caffeine and theobromine.

The methyl xanthines have desirable pharmacological effects. They act as stimulants, are anti-soporific, elevate mood, decrease fatigue, and increase the capacity to work.

The most studied methyl xanthine is caffeine. Caffeine is particularly useful to athletes and sports people. Graham (Sports Medicine 31, 787, 2001) after a study of the literature concluded that caffeine enables athletes to train at a greater power, with greater speed and for longer time. Thus, it increases power, speed and endurance in simulated and actual race conditions. It is also useful as an anti-soporific for young people who for social reasons wish to go to bed late and for people such as drivers who must stay awake. Caffeine also stimulates the metabolic rate and it is used in a number of preparations for weight reduction.

Because of these above-mentioned pharmacological properties, caffeine is an important ingredient in soft drinks such as the colas to which it is added on as a pure substance or as Guarana extract (Guarana is a plant indigenous to the Amazon basin which contains abundant caffeine and related alkaloids) or cola extract. One drink which has become extremely popular especially among young people is Red Bull$^{R\text{TM}}$ which in addition to caffeine contains taurine (which is a non-protein amino-acid occurring in high levels in the brain, retina and muscle tissue including heart muscle) and vitamins.

The half life of ingested caffeine in the human body is 5–6 hours which means that after one day there are only small quantities left in the circulation.

It is not obvious for those skilled in the art to formulate a drink which comprises each of creatine, creatinine and methyl xanthine.

Firstly, in order to obtain physiological value from a creatine drink containing, for example, a typical dose of 2–3 gms creatine, it requires several weeks' consumption of the drink: one drink has no significant effect. Over several weeks the creatine will accumulate in muscle as phosphocreatine and be available for energy production. In contrast, the opposite is true of caffeine- or other methyl xanthine-based drinks: the physiological effect from just one drink is immediate. Thus, creatine and methyl xanthines have very different pharmacokinetic profiles in the body.

Secondly, Vandeberg et al, (1996 J. Appl. Physiology 80, 452–457) found that caffeine counteracted the ergogenic action of muscle creatine loading, such that the two substances were antagonistic.

SUMMARY OF THE INVENTION

The present invention is concerned with the provision of compositions for human consumption comprising a methyl xanthine, creatinine and creatine or its derivatives, especially compositions presented in an aqueous medium, more especially compositions (such as drinks) in which creatine is provided in aqueous solution or in which creatine is suspended in an edible supporting matrix.

The term "creatine" as used herein is intended to encompass all bioavailable derivatives of creatine, such as creatine monohydrate, phosphocreatine, and other salts of creatine. Creatine monohydrate is particularly preferred. Accordingly the term "creatine" should be construed broadly where the context permits.

As explained above, it is well known that the creatine molecule in aqueous solution is unstable, especially at acidic pH (i.e. below pH 7), being converted to creatinine (Edgar & Shiver, 1925 J. Am. Chem. Soc., 47, p.1179–1188; Cannan & Shore 1928 Biochem. J. 22, p.920–929). This presents a problem in attempting to provide drinks or other compositions containing creatine in physiologically useful amounts, especially as drinks are usually formulated so as to have a pH below 7.

Edgar & Shiver conducted some investigations into the equilibrium which exists between creatine and creatinine in aqueous solution and, in particular, the effect on the equilibrium position by the use of buffers of different pH. Unfortunately the work of Edgar and Shiver does not offer any useful practical guidance to the person skilled in the art of formulating beverages and other nutritional compositions, for several reasons. Firstly, the publication by Edgar & Shiver is very old and of purely academic interest, would be unlikely to be consulted by a person skilled in the art of formulating beverages, and does not have a direct bearing on the formulation of beverages. Secondly, and most significantly, Edgar & Shiver conducted their experiments using extremely dilute solutions of creatine/creatinine (0.001 M, equivalent to 0.0149 g creatine/100 ml, creatine monohydrate having a molecular weight of 149): whilst these are appropriate for purely analytical considerations they have no relevance whatsoever to systems which comprise high concentrations (over 0.15 g creatine monohydrate or equivalent/100 ml) of creatine and are intended to provide physiologically useful amounts of creatine in a beverage. Thirdly, Edgar & Shiver neglected to take account of the change in pH which occurs upon conversion of creatine to creatinine and vice versa—such a change is probably negligible using the very dilute creatine/creatinine mixtures employed by Edgar & Shiver, but would have a significant impact at high concentrations, such as are desirable in a beverage, as the present inventors have discovered. Generally similar comments apply to the equally old publication by Cannan & Shore.

The obvious solution to the instability of creatine would be simply to increase the initial concentration of creatine in the composition, so that a physiologically useful amount of creatine is present in the composition for a longer time period. However this approach does nothing to prevent or inhibit the conversion of creatine to creatinine. Furthermore, extensive conversion of creatine to creatinine is likely to increase the pH of the composition, as the reaction involves the removal of a hydrogen ion. This may change the palatability and be undesirable to the consumer. Moreover, creatine is not particularly soluble in water (especially at the low temperatures, e.g. 3–5° C., at which drinks are usually stored), so there is a finite maximum initial concentration of creatine which cannot be exceeded. In addition, the inclusion of excess creatine is undesirable, as the presence of undissolved creatine in drink formulations is not attractive to consumers. Starting with a solution of creatine would result in a drink with less than the maximum amount of creatine in solution since some of the creatine would be converted to creatinine. The inventors have provided an alternative approach explained below.

In a first aspect the invention provides a composition for human consumption comprising creatine and a quantity of creatinine sufficient to render the creatine therein substantially stable (as defined below) in an aqueous medium, the composition further comprising a methyl xanthine. The creatinine content of the composition is present ab initio, (i.e. upon formation of the final composition), rather than arising during the storage of the composition as a result of the conversion of creatine into creatinine. It will be apparent from the teaching below that, at least in some embodiments, the production of the composition (i.e. processing prior to formation of the final compositions) may involve the deliberate conversion of creatine to creatinine. Stability of the creatine ab initio is desirable commercially, because it allows exact characterization of the creatine content of the composition (which may, for example, be indicated on packaging and the like) and it allows consumers to calculate the exact dose of creatine consumed.

The composition may be provided as a liquid, a semi-liquid, an edible matrix or a solid for subsequent solution in water. The creatine can be dissolved in water to provide a liquid.

For compositions in which the creatine is suspended in a semi-liquid or a supporting matrix the creatine content for the composition is preferably subjected to a micronisation process (e.g. crushing, pulverizing, powdering and the like) prior to incorporation into a semi-liquid or other supporting matrix so that the resulting composition is not unacceptably gritty in texture.

Conveniently the supporting matrix, if present, is a recognized foodstuff, such that a composition in accordance with the invention may take the form of an otherwise conventional foodstuff, supplemented with creatine and creatinine, such that solid creatine becomes suspended in the foodstuff. Examples of foodstuffs which may represent suitable supporting matrices for the composition of the invention include spreadable solids such as dairy or cheese spreads, margarines, caviar (mainly lump fish caviar) spread, and other fish pastes, meat spreads, and the like. Other convenient supporting matrices are those comprising sugars or other carbohydrates, such as liquid or solid honey, molasses, syrup (e.g. corn syrup, glucose syrup), treacle, glycerol or "Maxim Energy gel"™.

If desired the viscosity of the solution and/or the composition as a whole may be increased by the addition of viscosifiers, gelling agents and the like. Such components are well-known in the food industry and include, for example, plant-derived polysaccharides, gums and the like such as galactomannans, dextrans, guar gum, locust bean gum, xanthan gum and so on.

Such viscosifiers, gels and the like may take the form of a supporting matrix, if desired. One preferred edible matrix comprises a gel prepared from concentrated Aloe Vera extract: a smooth creamy paste (suitable for packaging in a squeezable tube) may be prepared by mixing 5 gms of creatine with (for example) 60 ml of a concentrated Aloe Vera gel (such as that obtainable from Aloe Commodities Int. Inc., Farmers Branch, Tex. 75234). Alternatively, or in addition, the supporting matrix may comprise a semi-liquid foodstuff such as a yogurt or other semi-liquid foodstuff.

The present inventors have previously found that the conversion of creatine to creatinine in aqueous solutions can be markedly inhibited by creatinine itself, such that a mixture of creatine and creatinine can quickly reach equilibrium and the creatine becomes substantially stable. Without wishing to be bound by any particular theory, the inventors believe that the explanation for this observation is that the conversion of creatine to creatinine is a reversible reaction. The inventors have now found that, by providing creatine in solution together with an appropriate amount of creatinine the conversion of creatine to creatinine (even in an acidic composition) can be greatly inhibited or even substantially prevented even at ambient (i.e. 2–39° C.) temperature or above for long periods (30 to 95 days or more). Thus, in some embodiments the composition as a whole may conveniently be selected to be acidic (i.e. have a pH below 7.0) or even alkaline (e.g. 7.0 to 8.5) without significantly adversely affecting the stability of the creatine content of the composition. In particular the composition desirably has a pH between 2.5 and 8.5, preferably between 3.0 and 7.0 and most preferably between 4.5 and 6.5.

Typically the composition has a pH in the range 4.5 to 5.5 which, to the human palate, has a refreshingly sharp taste without being too acidic.

Compositions in accordance with the invention are substantially stable so that creatine may be presented even in acidic formulations, contrary to the teaching of the art, in physiologically useful amounts, following storage for prolonged periods at ambient temperature. A physiologically effective amount of creatine is an amount sufficient to cause a measurable increase in the creatine content of the tissues of a subject following repeated consumption of the composition, relative to an initial baseline level. Methods of measuring the creatine content of the tissues of a subject are known (e.g. Harris, Hultman & Nordesjo (1974) Glycogen, glycolytic intermediates and high energy phosphates in biopsy samples of musculus quadriceps femoris of man at rest. Methods and variance of values. Scand. J. Clin. Lab. Invest. 33, 109–120; Dunnett, Harris & Orme (1991) Reverse phase ion-pairing high performance liquid chromatography of phosphocreatine, creatine and creatinine in equine muscle. Scand. J. Clin. Lab. Invest. 51, 137–141).

The term "substantially stable" is herein defined referring to a creatine/creatinine composition in which at least 75% (preferably at least 80%, and more preferably at least 85%) of the creatine in the composition immediately after formulation of the final product is unchanged, and therefore not converted into creatinine, for a period of at least (and preferably more than) 7 days storage. The stability of creatine depends on the pH; the latter decreases with increasing temperature. (The "final product" is the composition produced after all processing and production steps have been completed.)

The inventors have found that a 20° C. increase in temperature can decrease the pH by as much as 0.3 units. The temperature range to which the composition will be subjected (e.g. in a refrigerator or a warehouse) is typically between 2 to 50° C. Desirably, the composition will be sufficiently stable such that 75% of the creatine remains over the temperature range of 2 to 50° C. following a period of at least 30 days, more preferably 60 days, and most preferably at least 120 days, during storage. In order to specify stability it is necessary to specify the pH (which must be measured at the temperature at which the solution will be stored) at which stability is required. The pH is altered by warming or cooling of a buffered solution and over the range of temperatures that a solution may be stored the equilibrium ratio of creatine: creatinine can vary greatly. However, if the composition is stable at 50° C. then its creatine content will not decrease on storage at a lower temperature.

As mentioned above, the mole:mole ratio of creatinine to creatine to achieve stability of creatine, is found to depend on the pH of the solution and ranges from 1:2 for pH 7 to 3.8:1 for pH 4.25. It is preferred that the mole:mole ratio of creatinine to creatine is not more than 10:1. More preferred is a ratio of not more than 5:1. Most preferred is a ratio of creatinine to creatine which is not too high (since creatinine is an inactive ingredient) and the most preferred pH is 5 to 7 where the mole:mole ratio of creatinine to creatine ranges from about 1.2:1 to 1:2.

For the purpose of the invention, the creatinine can be added to the creatine as a pure substance or the creatinine can be manufactured in situ by heating creatine in solution, preferably at low pH (e.g. pH 2 to 3). It is most convenient for the solution to be heated and held for at least 30 minutes at 90° C. or more because these are the conditions often used for the sterilization of a liquid for commercial sale. (Alternatively, an equivalent sterilizing "heat dose" can be provided by heating to greater temperatures for shorter periods of time or vice versa.) In other embodiments, creatinine can be prepared by heating a solution of creatine for several hours at pH 2 to 3 and then adding it to a solution of creatine at higher pH (e.g. pH 7) and adjusting the final mix to the desired pH (e.g. pH 5). If required the solution can then be re-sterilized under the above-mentioned conditions. In this method of preparation, there may be little or no further conversion of creatine to creatinine and stability is ensured immediately after mixing the two solutions. This method has advantages because creatine is not very soluble in water when chilled in a refrigerator, whereas creatinine is much more soluble. By producing a stable solution of creatine by this method it is possible to formulate a drink which contains a relatively larger quantity of stable creatine than could be achieved otherwise. Thus by this means, it is possible to produce a drink suitable for refrigeration which contains up to 0.8 g creatine/100 ml or a drink suitable for storage at ambient temperatures of 18 to 25° C. which contains up to about 1.5 g creatine/100 ml (or about 1.7 g creatine monohydrate/100 ml).

A further advantage of the invention is that it enables the provision of a composition which comprises the maximum concentration of dissolved creatine available (under the relevant conditions of pH and temperature), but using the least amount of creatine necessary, in a stable formulation, and so does not require the use of excess creatine.

A preferred embodiment of the invention is an aqueous drink, especially one at acid pH (i.e. below pH 7), and in particular which has a pH in the range 4–6.5, especially 4.5–5.5, and which comprises at least 0.15 g creatine (or creatine monohydrate and the like) per 100 ml. Preferably the drink comprises at least 0.3 g creatine (or creatine monohydrate and the like) per 100 ml, more preferably at least 0.4 g per 100 ml and most preferably at least 0.5 g per 100 ml.

At low temperature (4° C.) creatine is not especially soluble (abut 0.8 gms/100 ml) in water. At room temperature (20° C.), the solubility of creatine in water is a little higher (about 1.2 gms/100 ml). Thus, for a 500 ml drink the maximum dose of soluble creatine will be about 4 gms (and 2 gms for a 250 ml drink) if refrigerated. For a drink at room temperature, the maximum soluble creatine dose will be about 50% higher.

The composition of the invention also comprises a methyl xanthine, such as caffeine, theobromine or theophylline. Although theophylline is extremely active, and commercially available as a pure compound, it is primarily used in the management of asthma and is generally thought of as a pharmaceutical. Accordingly, caffeine and theobromine are preferred, relative to theophylline, for inclusion in the composition of the invention. Of these, caffeine is preferred to theobromine, being more active.

A typical cup of instant coffee (6 oz.) contains about 100 milligrams caffeine. It is considered 1000 mg caffeine would be the absolute upper limit of sensible intake in a single dose or drink. Since very small doses (25 milligrams to 50 milligrams a day) can have an effect, the lower limit should be set at 10 milligrams. (Theobromine is less active than caffeine, theophylline is more active.)

Thus the dose range per drink for methyl xanthines is 10–1000 milligrams. Preferred is a dose range of 100–300 milligrams. Most preferred is about 200 milligrams.

The composition may comprise a solution of a methyl xanthine, creatine and creatinine in water without additional components (such as for example flavoring) as a solution in water, e.g. mineral water or carbonated water, using processes which are well known to those skilled in the art.

Preferably however the composition may comprise one or more further components to improve its palatability, stability, flavor or nutritive quality. These further components may include electrolytes, or may be selected from the group consisting of: vitamins, lipids, proteins, carbohydrates, polyols (such as ethylene glycol, glycerol, sorbitol etc.), amino acids, trace elements, colorings, flavors, artificial sweeteners, natural health and performance improving substances, anti-oxidants, stabilizers, preservatives, and buffers.

In particular preferred embodiments the invention provides an "energy drink". This may be similar to existing methyl xanthine-containing drinks (such as Red Bull$^{R}$™ or cola drinks) but containing added creatine and creatinine. Existing cola drinks and Red Bull$^{R}$™ are generally very acidic (about pH 3.5). Such a low pH is not ideal for a creatine-containing drink, as very large amounts of creatinine would have to be added in order to stabilize the creatine content. Thus a composition in accordance with the invention would preferably have a higher pH than Red Bull$^{R}$™ or conventional cola drinks (e.g. about pH 4.4 for a carbonated drink or about pH 6.0 for a still drink). This also has the advantage of providing a drink which is less likely to induce dental caries. A drink in accordance with the present invention may comprise taurine (or a salt thereof). The dose of taurine included in supplements is about 100–200 milligrams per dose. A preferred dose range of taurine for a drink in accordance with the invention is 25–1000 milligrams, more preferably 50–300 milligrams, most preferably about 200 milligrams.

An alternative embodiment is to provide a drink comprising creatine and creatinine which is more similar to older, more traditional, methyl xanthine stimulant-containing drinks, such as coffee, tea or cocoa. Cocoa-based drinks (i.e. those containing an extract obtained from cocoa pods) will preferably comprise milk (which expression encompasses whole milk, semi-skimmed milk, skimmed milk, condensed milk and reconstituted milk made using milk powder). Coffee-based drinks (i.e. those containing an extract obtained from coffee beans) could be made with or without milk. Tea-based drinks (i.e. those containing an extract obtained from leaves of the tea plant) may similarly be made with or without milk. The tea may be black tea (i.e. made with an extract obtained from fermented tea leaves) or green tea (i.e. made with an extract obtained from unfermented tea leaves). The pH of drinks of this sort will preferably be above 5.0, typically about pH 6.0, although citrus tea drinks (i.e. tea-based drinks flavored with citrus fruit, especially lemon juice) may have a lower pH, about 4.5.

Vitamins may be included with advantage in the composition of the invention. These may be added in amounts which range from 20 to 100% of their recommended daily allowance (RDA). The following are typical of those which are useful: vitamin E, vitamin C, thiamin, riboflavin, niacin, vitamin B6, folacin, vitamin B12, biotin, and pantothenic acid.

In some cases a lipid component may be desirable. The protein content (if any) may be present as soya or milk proteins (e.g. whey or casein). The carbohydrate content (if any) or the composition may be present as starch (particularly soluble starch) and/or sugars. The sugars which may be present in the composition include glucose, fructose, sucrose, lactose and maltose.

Artificial sweeteners which can be used include Aspartame, Acesulfam K, Saccharin and Cyclamate. Almost any desired flavoring can be added, most preferably fruity flavors such as berry, lemon, orange, papaya and grapefruit. However, at less acidic pHs (e.g. over 5.0) other flavors such as chocolate, malt, caramel and other flavors suitable for "milky" drinks can be used. Citric acid may also be used as an acidulant and citrate and phosphate (e.g. sodium citrate or phosphate) as a buffering agent. Other buffering agents may be used to regulate the acidity of the drink. Also other natural health improving substances may be added in physiologically active amounts. The following are typical of those which are useful: Pau D'Arco tea, Ginseng, Suma tea, Ginkgo, bee pollen, myrrh, hydroxy-methy-butyrate, glutamine, di- tri-, and polypeptides containing glutamine, ribose, caffeine, and lipoic acid.

Preservatives can be provided typically by potassium benzoate and/or potassium sorbate.

Coloring can be provided, typically by using a cold water soluble colorant such as beta-carotene. Other suitable colorings will be apparent to those skilled in the art.

A clouding agent may be included in the composition, if desired, to improve the appearance of the composition.

The mineral and trace elements can also be added in any type or form which is suitable for human consumption. It is convenient to provide the calcium and potassium in the form of their gluconates, phosphates or hydrogen phosphates, and magnesium as the oxide or carbonate, chromium as chromium picolinate, selenium as sodium selenite or selenate, and zinc as zinc gluconate. Typically the amounts are: sodium at 400 mg/liter, calcium at 100 mg/liter, chloride at 600 mg/liter, potassium at 200 mg/liter, magnesium at 75 mg/liter and phosphorus at 50 mg/liter, chromium at 125 mg/liter, selenium at 125 mg/liter and zinc at 15 mg/liter.

For liquid drinks in which the creatine is completely soluble, the amount of creatine (calculated as the monohydrate from hereon) per litre or per Kg of prepared composition may range from 1.5 g to 24 g with a preferred content of about 12 g per liter. The normal serving size is in the range 200–750 ml, providing about 2 to 7 g, preferably about 5 g of creatine. During the first 4 days of creatine supplementation the recommended consumption is about 2.0 liters per day, divided in 4 or 5 parts per day to achieve creatine saturation. This is followed by 1 serving of 250–750 ml per day containing about 2–3 g of creatine to provide a sufficient level of creatine to maintain saturation.

For suspensions of creatine in semi-liquid or other edible supporting matrices, the amount of creatine per 100 g may range from 1 to 80 g (calculated as creatine monohydrate from hereon) The preferred portion size is in the range 5 to 100 g providing between 2 to 10 g (preferably 5 g) of creatine. During the first four days of creatine supplementation the recommended consumption is a suspension containing 10 to 25 g per day divided into 4 or 5 parts per day to achieve maximum creatine elevation in the tissues. However lower doses over a longer period (e.g. 3 g daily for 4 weeks) will have the same effect. This is followed by one serving of suspension daily containing 3 to 5 g creatine to provide a maintenance level of creatine.

The invention also relates to a method of making the composition defined above. Thus, in a second aspect the invention provides a method of making a composition for human consumption, the method comprising the step of providing, in the same composition, a methyl xanthine, creatine and sufficient creatinine to render the creatine substantially stable (as herein defined) when the composition is mixed with an aqueous medium. Preferably the aqueous medium is water or an aqueous solution. The method will also normally include the step of providing water or an aqueous solution, preferably in sufficient amount so as to dissolve substantially all of the methyl xanthine, creatine and creatinine in the composition.

It will be apparent to those skilled in the art that the order of addition of the components to the composition is generally not significant, and any sequence of steps which provides the object of the invention will suffice. Thus, for example, solid methyl xanthine, solid creatine and solid creatinine may be added (simultaneously or separately) to water or an aqueous medium; or water or an aqueous medium may be added to solid methyl xanthine, creatine and/or creatinine.

Accordingly, in one embodiment the second aspect of the invention provides a method of preparing a creatine containing composition for human consumption in which the creatine is substantially stable (as herein defined), the method comprising the steps of: providing a solution of creatine; and subjecting the solution of creatine to suitable conditions so as partially to convert the creatine to creatinine, thereby forming sufficient creatinine to render the creatine in the resulting composition substantially stable (as herein defined) and adding (at any stage) an amount of methyl xanthine. The method typically will comprise the further step of packaging the composition in suitable containers e.g. glass or plastic bottles, foil sachets, aluminum cans etc.

Preferably the method is such that subjecting the solution of creatine to suitable conditions involves heating the solution above average ambient temperature. In one preferred method, the solution is heated to 90° C. for 30 minutes.

In a third aspect the invention provides a method of preparing a creatine containing composition for human consumption in which the creatine is substantially stable (as herein defined), the method comprising the steps of: providing a solution of creatine; providing a solution of creatinine; and mixing the solutions so as to form a resulting composition in which there is sufficient creatinine to render the creatine substantially stable (as herein defined), and adding (at any stage) an amount of methyl xanthine.

In this method the pH of the solution of creatinine is preferably lower than the pH of the solution of creatine. Desirably the pH of the solution of creatinine is in the range 2 to 3, and the pH of the solution of creatine is preferably in the range 4.5 to 7 with adjustment, if necessary, of the final pH to the desired level.

In a fourth aspect the invention provides a method of preparing a creatine containing composition for human consumption in which the creatine is substantially stable (as herein defined), the method comprising the steps of: providing solid creatine; providing solid creatinine; and mixing the two solids so as to provide a resulting composition which, when dissolved in aqueous solution, provides a composition in which there is sufficient creatinine to render the creatine substantially stable (as herein defined), and adding (at any stage) an amount of methyl xanthine. Typically this method will further comprise the step of adding sufficient water or aqueous solvent to substantially dissolve the resulting composition. If desired the water or aqueous solvent may be pre-sterilized by heat treatment and/or filtration.

In a fifth aspect, the invention provides a method of preparing a creatine containing composition for human consumption in which the creatine is substantially stable (as herein defined), the method comprising the steps of: providing solid creatine and solid creatinine, or an aqueous solution of creatinine, the creatinine being in sufficient quantity to render the creatine substantially stable (as herein defined); mixing the solid creatine with the solid creatinine or aqueous solution of creatinine; adding (at any stage) an amount of methyl xanthine; and adding to the mixture an edible supporting matrix.

It will be appreciated that the methods of the invention may involve addition of a methyl xanthine as a substantially pure substance, or as part of a mixture. In particular the methyl xanthine may be added as a constituent of a plant extract, especially a caffeine-containing and/or theobromine-containing plant extract (e.g. an extract obtained from tea leaves, and/or coffee beans, and/or cocoa pods).

Advantageously, performance of the methods of the second, third, fourth or fifth aspects will result in a composition in accordance with the first aspect defined above.

$$y=-0.001x^7+0.077x^6-1.693x^5+20.594x^4-149.615x^3+649.397x^2-1560.343x+1603.236$$

$$r==1.000$$

DETAILED DESCRIPTION OF THE INVENTION

The present invention is demonstrated by the following non-limiting examples and related figures.

EXAMPLE 1

This example relates to a convenient in vitro assay method for determining the concentration of creatine in a solution.

1. The pH of each solution was determined with a pH meter.
2. Mixtures were stored in a dark cabinet at ambient temperature (circa 22° C.) in a laboratory.
3. 2–3 ml of solution were sampled after periods of time between 0 and 124 days and stored frozen at −30° C. until analyzed immediately or within one to two days.
4. Thawed samples were dissolved in distilled water to give a suitable dilution and the creatine concentration of each was determined by the method of Harris et al, (Scand. J. Clin. Lab. Invest. 33, 1974, 109–120). Briefly, the assay was performed in the presence of (final concentration) 100 mM triethanolamine buffer pH 8.5; 10 mM magnesium acetate; 1 mM EDTA; 30 mM KCl; 1 mM phosphoenolpyruvate; 2 mM adenosinetriphosphate (ATP); 0.18 mM nicotinamide-adenine-dinucleotide/reduced form (NADH); creatine kinase (CK); pyruvate kinase (PK), and lactate dehydrogenase (LDH). The concentration of creatine was determined from the oxidation of NADH measured photometrically at 340 nm.

| | |
|---|---|
| CK: Cr + ATP → | PCr + ADP |
| PK: ADP + PEP → | ATP + Pyruvate |
| LDH: Pyruvate + NADH → | Lactate + NAD |

EXAMPLE 2

The object of this trial was to determine the stability of creatine when heated at 90° C. at different pH's and the solutions left at room temperature for up to 124 days. At 90° C. the conversion of creatine to creatinine generally occurs very rapidly.

Solutions in water of 2 g creatine monohydrate in 100 ml 0.1 M citric acid-0.1 M potassium phosphate buffers at pH's 3, 4, 5, 6 and 7 were heated at 90° C. for 30 minutes. The solutions were quickly cooled, the pH (which had changed) re-measured and then left at room temperature as described in Example 1. Aliquots were taken after 7, 15, 29, 43, 57, 89 and 124 days and stored at −30° C. and subsequently analyzed for creatine. The pH of each sample was measured. The concentration of creatinine was estimated from the difference between the starting level (2 g creatine monohydrate) and the measured level of creatine (calculated as the monohydrate).

Results

Figure 1:
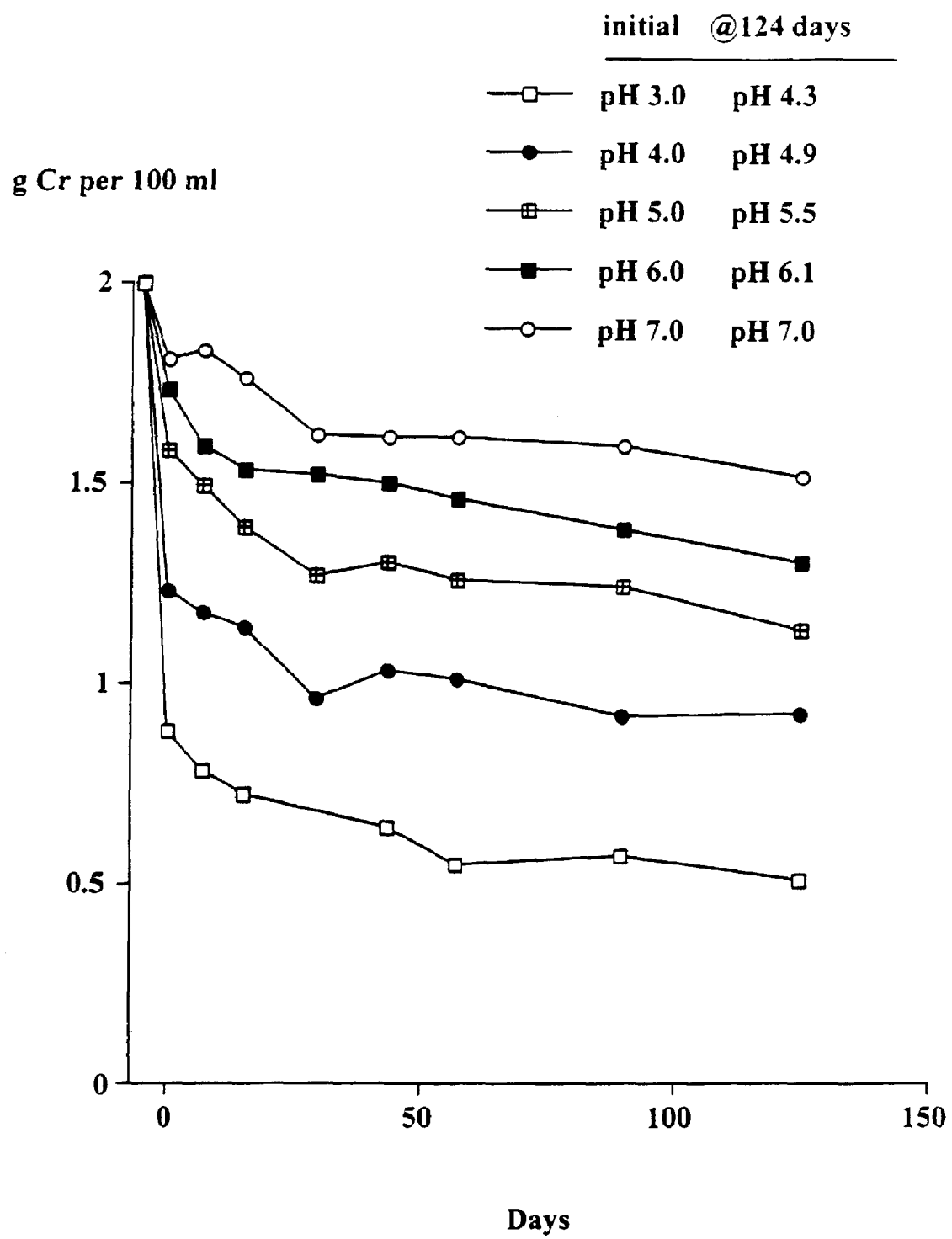
FIGS. 1 and 2 are graphs of the creatine concentration (as g per 100 ml, and as a percent of the initial concentration, respectively) in solutions of different pH against time (as described in Example 2)
Figure 2:
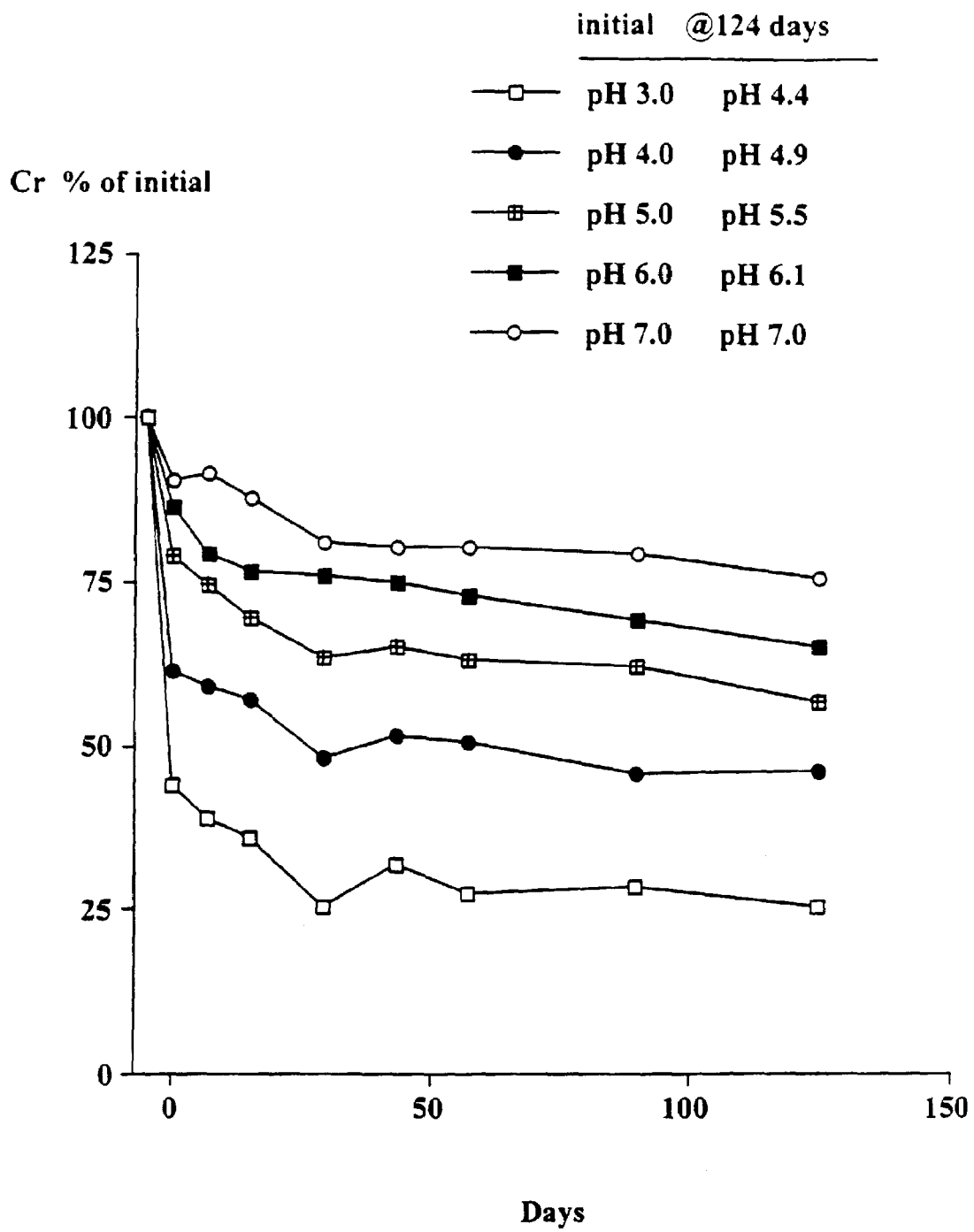
Figure 3:
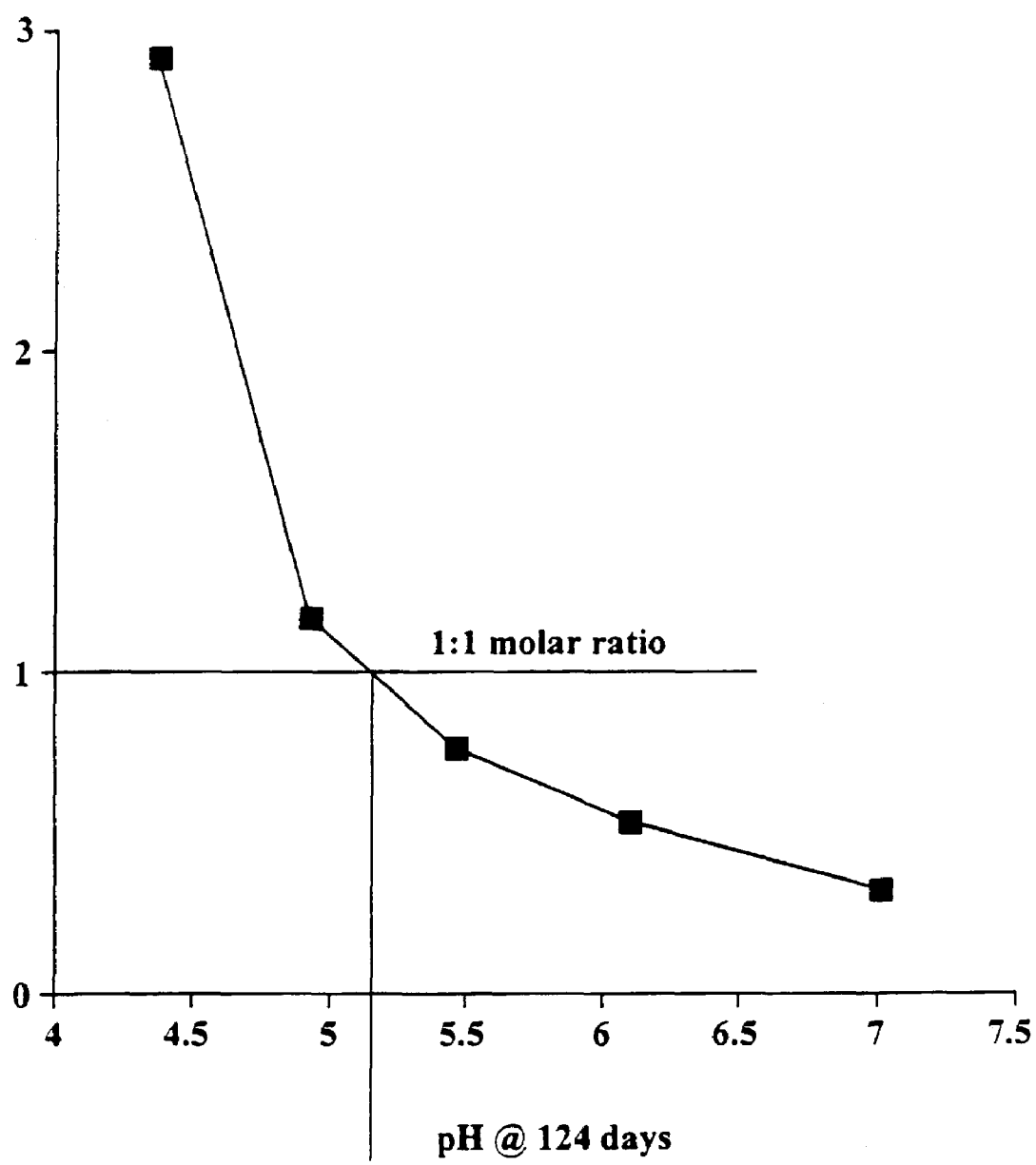
FIG. 3 is a graph of the mole:mole ratio of creatinine (Cn) to creatine (Cr) in solutions of different pH's after 124 days incubation (as described in Example 2)

As shown in FIGS. 1 and 2, there was a rapid conversion of creatine to creatinine after the 30 minutes heating. However, the extent of conversion depended upon the pH of the solution, being progressively greater with the lower pH. On storage for 30 days a further decline in the creatine concentration occurred. Between 30 and 124 days the level of creatine reached stability at all pH's. FIG. 3 shows the mole:mole ratio of creatinine and creatine at day 124 (17.7 weeks) at different pH's from which it was possible to estimate the amount of creatinine required to render the creatine maximally stable.

Conclusion

Starting with a composition comprising creatine and no creatinine it takes 4 weeks or more for solutions incubated at 22° C. to reach stability. The time taken to reach stability increases the lower the pH since more creatine must be converted to creatinine. The amount of creatinine required to render a solution of creatine stable depends on the pH of the solution. Generally, the amount of creatinine required increases with decreasing pH. However, at each pH it is possible to predict the ratio of creatinine to creatine which would achieve maximum stability.

EXAMPLE 3

The object of this trial was to determine the effect of creatinine in the proportion of 1:1 (w/w) to creatine monohydrate on the stability of creatine at different pHs after heating the mixture for 30 minutes at 90° C.

Quantities of 1.5 g creatine monohydrate and 1.5 g creatinine were dissolved in 100 ml of 0.2 M citrate-0.2 M potassium phosphate buffers at pH's 3, 4, 5, 6 and 7. The solutions were heated at 90° C. for 30 minutes, cooled, the pH re-measured and left at ambient temperature (22° C.) for up to 95 days.

Results

Figure 4:
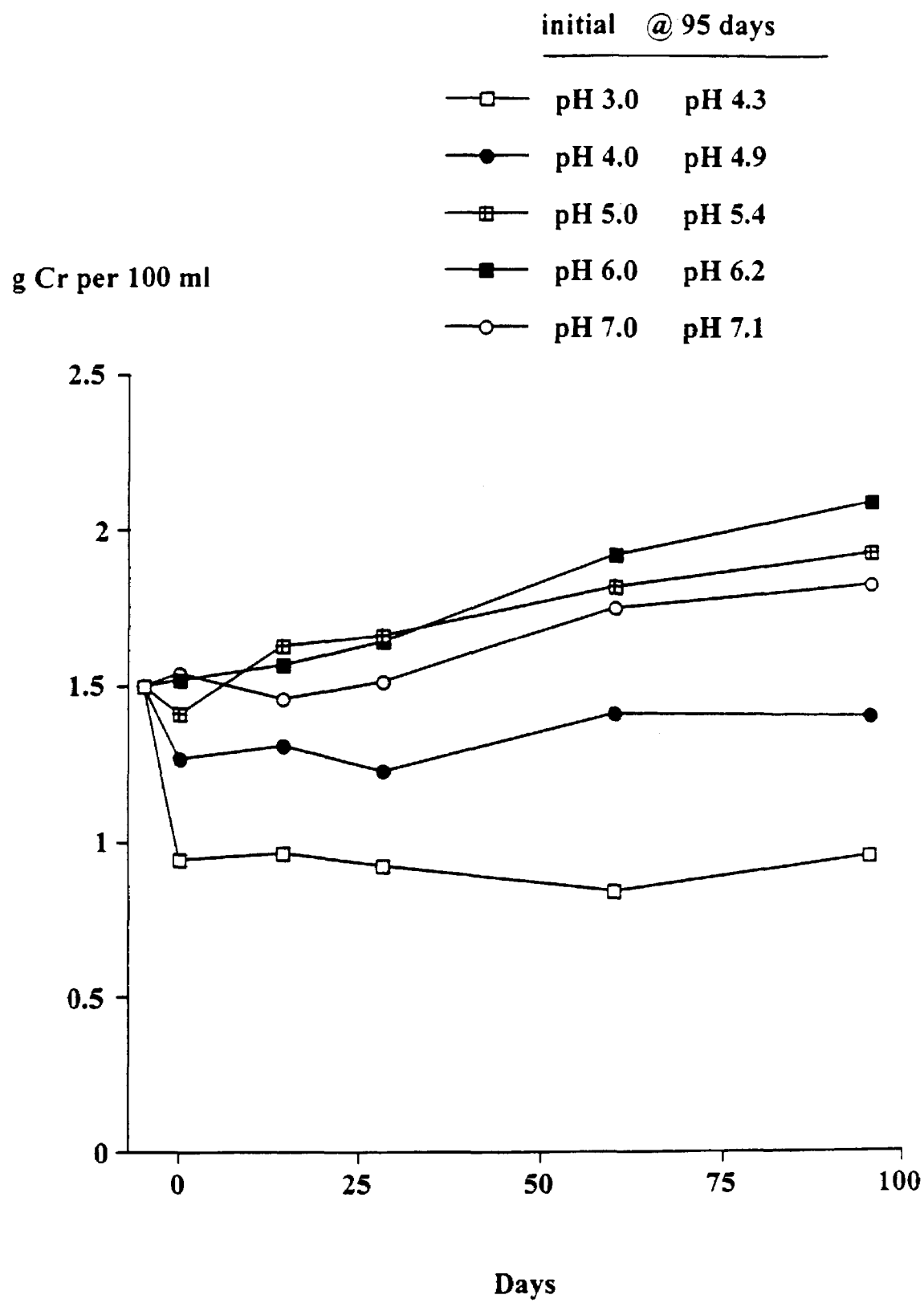
FIGS. 4 and 5 are graphs of a creatine concentration (as g per 100 ml, and as a percent of the initial concentration, respectively) against time, where a mixture of creatine and creatinine in solutions of different pH's were incubated for up to 95 days (as described in Example 3)
Figure 5:
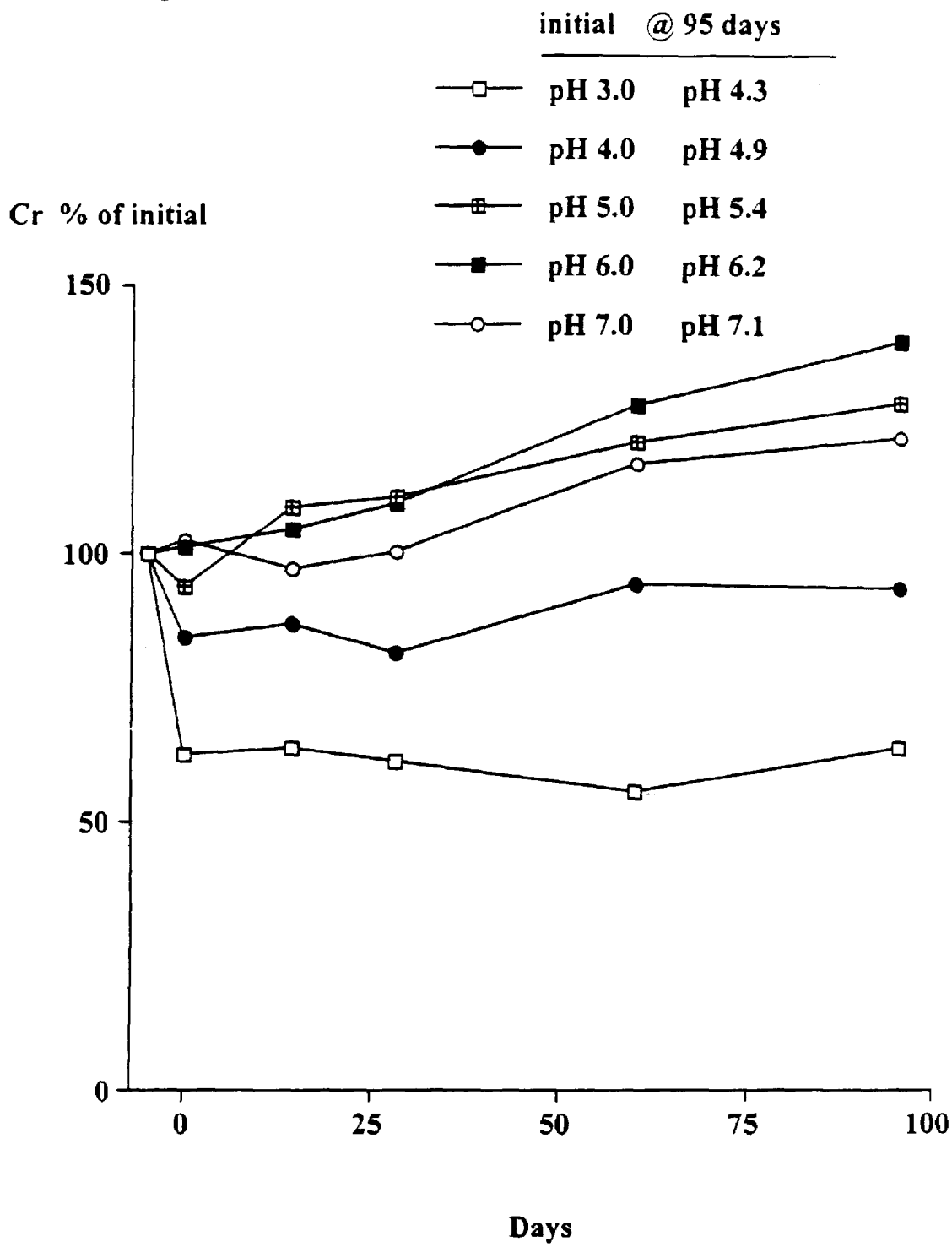

As shown in FIGS. 4 and 5, at pH's 6 and 7 there was no loss of creatine during the heating period. Small but progressively greater losses occurred at pH 5, 4 and 3 with time.

Creatine stability occurred at all pH's. At pH's 5, 6 and 7 there was even a trend for the creatine concentration to increase.

Conclusions

In the presence of a sufficient quantity of creatine (which for pH's 5, 6 and 7 was equal to or less than a weight ratio creatinine: creatine monohydrate of 1:1), creatine is exceptionally stable, even when heated for 30 minutes at 90° C. With an insufficient quantity of creatinine (for samples at pH's 3 and 4) heating for 30 minutes at 90° C. resulted in production of sufficient creatinine also to render the remaining creatine stable for at least 95 days thereafter.

EXAMPLE 4

This example illustrates a method of heating a solution of creatine to form creatinine and then adding it to a flavored drink containing creatine to give a concentration which is substantially stable. Simultaneously it is desired that the concentration of creatine remaining is close to its maximum solubility such that it will not precipitate out in the refrigerator at 3° C. This is a requirement for most beverages since they may be chilled in a refrigerator before consumption.

Step 1

5 g of creatine monohydrate were dissolved in 100 ml 0.1 M citric acid (pH 3) and heated at 90° C. for two hours. This converted most of the creatine into creatinine. The solution was cooled to room temperature.

Step 2

A solution was prepared containing 5 g creatine monohydrate in 650 ml 0.1 M citrate buffer at pH 5 at room temperature, without heating. In addition, the solution contained 15 percent Aloe Vera juice, flavoring and dextrose to sweeten.

Step 3

Solutions from steps 1 and 2 were then mixed together and heated at 90° C. for 30 minutes to sterilize the mixture and then placed in a glass or plastic bottle and stored at 22° C. The 5 g creatine monohydrate added in step 2, remained substantially stable upon formulation of the final product.

The above drink when placed in refrigerator at 3° C. did not precipitate out creatine. In the presence of creatinine it was found that the maximum solubility of creatine in a refrigerator at 3° C. is about 1.2 g/100 ml (equivalent to circa 1.4 g creatine monohydrate).

EXAMPLE 5

It is well known to those skilled in the art that when buffered solutions are heated the pH decreases. Thus a 0.1 to 0.2 M citrate-phosphate buffer with a pH of 4.75 at 20° C. will on warming to 40° C. change to pH 4.5. Conversely cooling a buffered solution will increase its pH. These changes in pH will affect the mole:mole ratio of creatine: creatinine necessary to achieve stability in accordance with the relationship illustrated graphically in FIG. 3. Thus the ratio will change from about 1.7:1 at pH 4.75 to 2.5:1 at pH 4.5. Thus a composition which is stable at 20° C. will be changed to a new stable composition when stored at 40° C. The object of this example is to establish and compare the ratios required for stability at 2° C., 22° C. and 39° C. over a range of pHs encompassing 3.8 to 8.25.

Protocol 1. 0.2 M citric acid–0.2 M potassium phosphate buffers at pH's 3.8 and 8.25 were prepared.

2. Using solutions from 1. above the following solutions were prepared at room temperature:

a) 67.06 mM creatine monohydrate in buffer at pH 3.8 (1 g in 100 ml)

b) 67.06 mM creatinine in buffer at pH 3.8 (0.758 g in 100 ml)

c) 67.06 mM creatine monohydrate in buffer at pH 8.25 (1 g in 100 ml)

d) 67.06 mM creatinine in buffer at pH 8.25 (0.758 g in 100 ml)

3. Solutions 2a and 2c were mixed in various proportions to obtain solutions of 67.06 mM creatine monohydrate with pH values as follows:

3.8, 4.0, 4.2, 4.4, 4.6, 4.8, 5.0, 5.2. 5.4, 5.6, 5.8,
6.0, 6.25, 6.5, 6.75, 7.0. 7.25, 7.5, 7.75, 8.0, 8.25

4. Similarly, solutions 2b and 2d were mixed in various proportions to obtain solutions of 67.06 mM creatinine at the same pH values identified in 3 above.

5. Solutions of creatine monohydrate and creatinine from steps 3 and 4 were mixed, to form solutions of the correct pH values necessary to produce the mole:mole creatinine to creatine ratios shown in Table 1 (initially derived from FIG. 3), in a final volume of 10 ml in a glass screw cap tube. Triplicate samples were prepared.

6. The samples were capped and heat sterilized for 30 minutes at 90° C.

7. One set of samples was stored at 2° C., another set at 22° C. and the final set stored at 39°.

8. Aliquots were taken after 5 and 6 weeks for pH measurement and analysis of creatine by the enzymic method described in Example 1 and on the 6th week samples for creatinine by the alkaline picrate method (using the "Creatinine Diagnostic Kit" end-point method; kit supplied by Sigma-Aldrich Company Limited, Poole, Dorset, UK). Despite the chemical similarity of creatine and creatinine, the former does not give any reaction with the alkaline picrate method.

TABLE 1

Mole:mole ratios of creatinine to creatine initially added in example 5
(in all cases the final total concentration of
creatinine + creatine is 67.06 mm.)

| Incubation temperature | 2° C. | 22° C. | 39° C. |
|---|---|---|---|
| Starting pH = | | | |
| 3.8 | ∞/1 | ∞/1 | ∞/1 |
| 4.0 | 3.90/1 | ∞/1 | ∞/1 |
| 4.2 | 2.75/1 | 3.90/1 | ∞/1 |
| 4.4 | 2.10/1 | 2.75/1 | 3.90/1 |
| 4.6 | 1.55/1 | 2.10/1 | 2.75/1 |
| 4.8 | 1.12/1 | 1.55/1 | 2.10/1 |

TABLE 1-continued

Mole:mole ratios of creatinine to creatine initially added in example 5 (in all cases the final total concentration of creatinine + creatine is 67.06 mm.)

| Incubation temperature | 2° C. | 22° C. | 39° C. |
|---|---|---|---|
| 5.0 | 0.92/1 | 1.12/1 | 1.55/1 |
| 5.2 | 0.80/1 | 0.92/1 | 1.12/1 |
| 5.4 | 0.70/1 | 0.80/1 | 0.92/1 |
| 5.6 | 0.62/1 | 0.70/1 | 0.80/1 |
| 5.8 | 0.56/1 | 0.62/1 | 0.70/1 |
| 6.0 | 0.49/1 | 0.56/1 | 0.62/1 |
| 6.25 | 0.43/1 | 0.49/1 | 0.56/1 |
| 6.5 | 0.38/1 | 0.43/1 | 0.49/1 |
| 6.75 | 0.335/1 | 0.38/1 | 0.43/1 |
| 7.0 | 0.30/1 | 0.335/1 | 0.38/1 |
| 7.25 | 0.27/1 | 0.30/1 | 0.335/1 |
| 7.5 | 0.24/1 | 0.27/1 | 0.30/1 |
| 7.75 | 0.21/1 | 0.24/1 | 0.27/1 |
| 8.0 | 0.18/1 | 0.21/1 | 0.24/1 |
| 8.25 | 0.15/1 | 0.18/1 | 0.21/1 |

Results

Analysis of the creatine content of samples from the solutions incubated at 39° C. showed no significant change between weeks 5 and 6. The mean change in concentration was +0.76 (SD 1.3) mmol/l corresponding to an increase of just 0.113 g of creatine monohydrate per litre. The percentage change from weeks 5 and 6 in these samples was 3.1 (3.8)% which is of the same order as the analytical error of the method.

Figure 6:
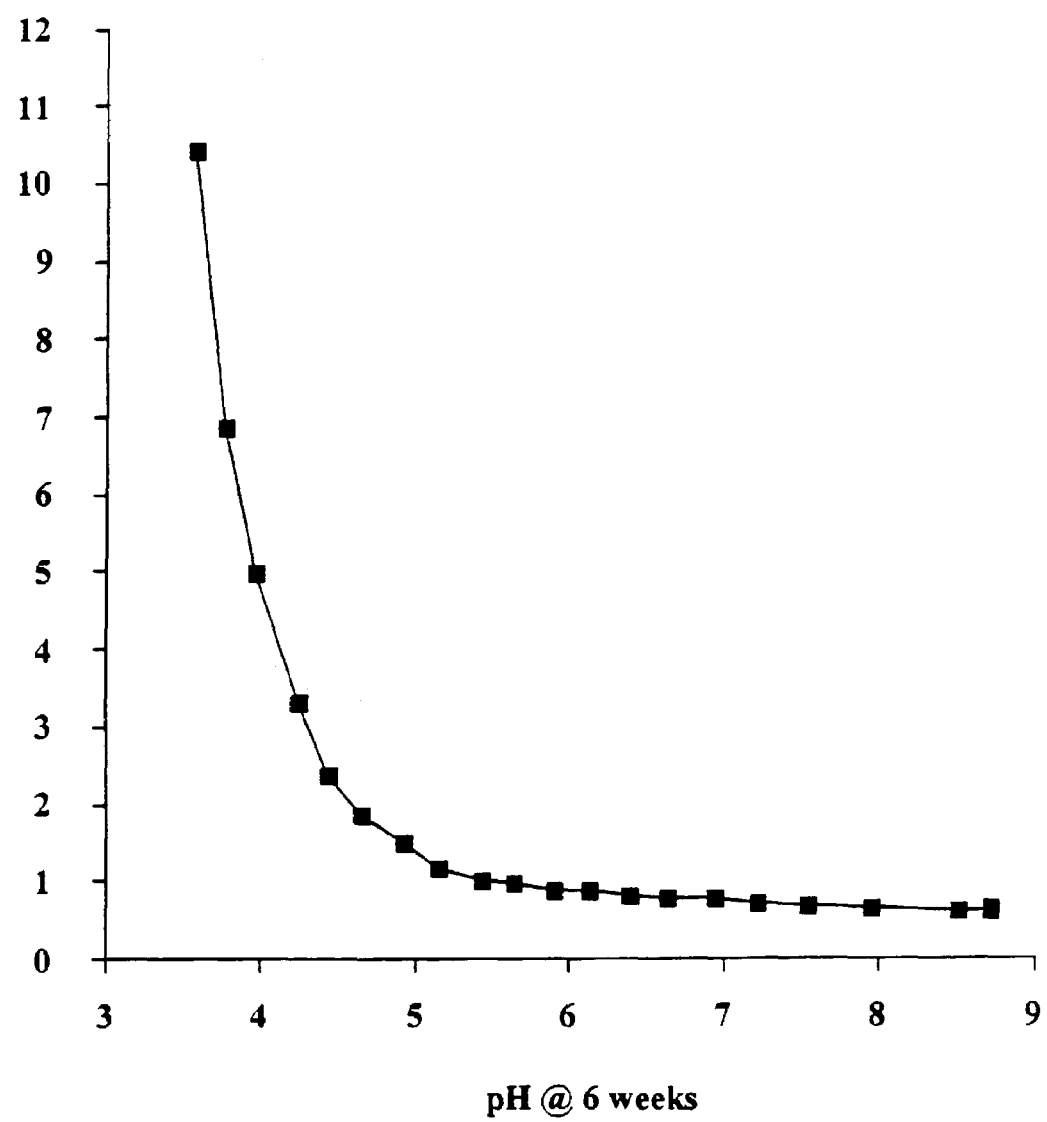
FIG. 6 is a graph of the mole:mole ratio of creatinine to creatine against pH for solutions stable after 6 weeks incubation at 39° C. (as described in Example 5)

As shown in FIG. 6, at 39° C. the creatinine to creatine ratio increases rapidly in samples where the final pH is between 4.6 (circa 2.1:1) and 3.7 (circa 10.0:1). Between pH 5.2 and 8.8 the ratio is equal to or below 1.0. At pH's greater than 6.0 the ratio decreases approximately linearly from 0.9 to a ratio at pH 8.8 of 0.6:

Despite starting at the same pH and with equal concentrations of creatine and creatinine, there were clear differences in pH at the end of 6 weeks incubation at 2, 22 and 39° C. (Table 2).° the highest pH. The final pH attained is the direct result of:

a) The immediate effect of temperature on the hydrogen ion activity of the solutions, since increasing temperature causes a decrease in pH; and b) The effect of conversion of creatine to creatinine, a process which removes hydrogen ions raising the pH, or, conversion of creatinine to creatine which releases hydrogen ions and causes a decrease in pH, until equilibrium is attained between the concentrations of creatine and creatinine. The extent of any change will depend upon how far the initial concentrations of creatine and creatinine are from those at equilibrium and will be greatest when starting with either creatine or creatinine alone (as in Example 2). This can be a slow process and, as shown in FIG. 2, may take up to 8 weeks with a solution of low pH, composed initially of just creatine. (As the incubation temperature in Example 2 was 22° C. then a slightly shorter time to reach equilibrium would be expected at 39° C.) The magnitude of the change in pH caused by the interconversion of creatine and creatinine is dependent upon the absolute concentrations of creatine and creatinine, as well as the buffering capacity of the media used. However, a knowledge of these factors enables solutions of known final compositions of creatine and creatinine and pH to be prepared.

TABLE 2

The effect of temperature upon the pH of a solution of creatine and creatinine of 67 mmol/l (combined concentration) made up in 0.2 M citric acid-potassium phosphate buffers, after 6 weeks incubation to allow attainment of equilibrium.

| | pH | | |
|---|---|---|---|
| No | @ 2° C. | @ 22° C. | @ 39° C. |
| 1 | 4.0 | 3.7 | 3.6 |
| 2 | 4.5 | 4.2 | 4.0 |
| 3 | 4.9 | 4.6 | 4.4 |
| 4 | 5.1 | 4.8 | 4.7 |
| 5 | 5.3 | 5.0 | 4.9 |
| 6 | 5.5 | 5.2 | 5.2 |
| 7 | 6.1 | 5.8 | 5.9 |
| 8 | 6.5 | 6.3 | 6.4 |

(the starting pH value was essentially as that indicated for the samples incubated at 22° C.).

Figure 7:
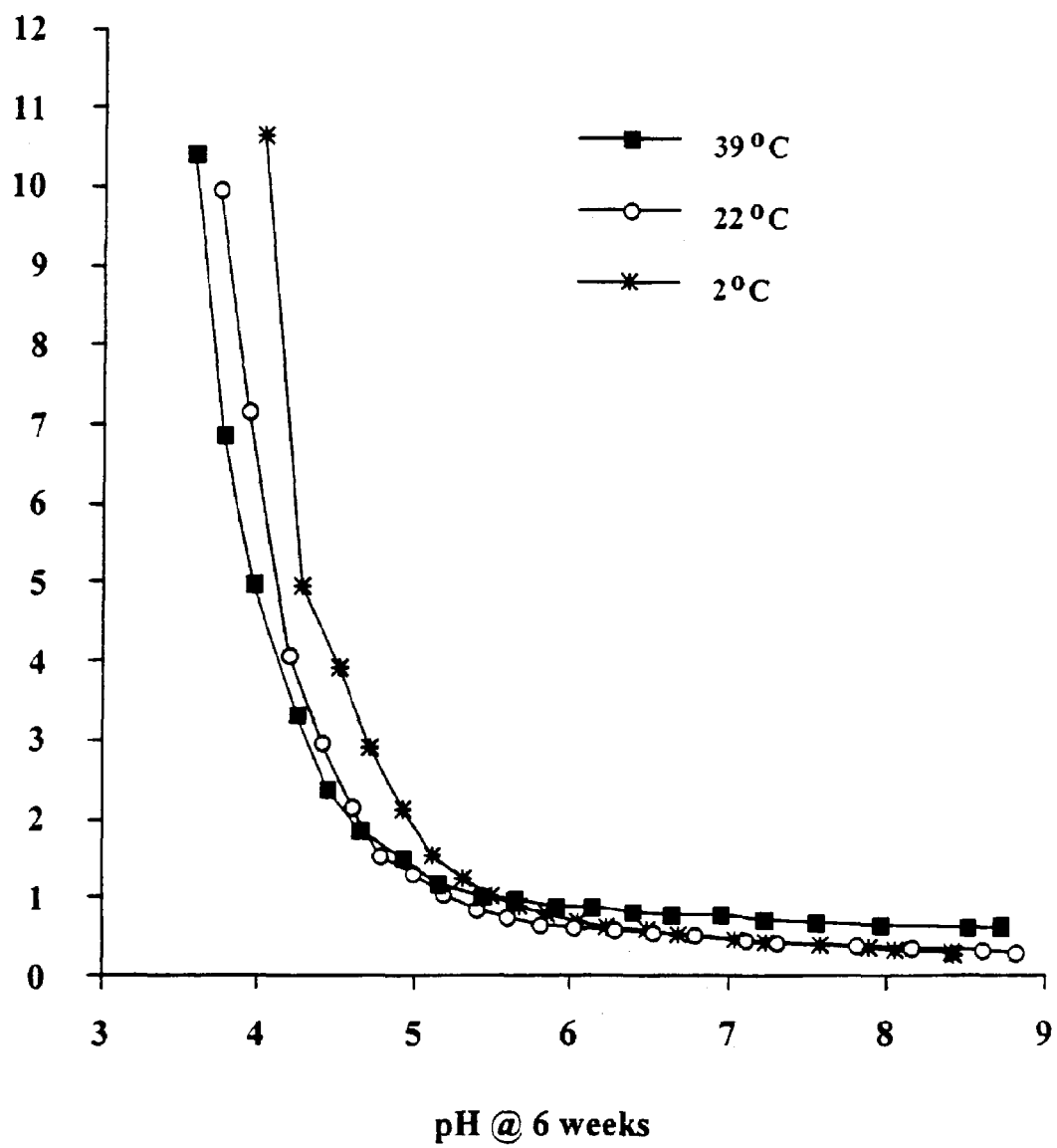
FIG. 7 is a graph of the mole:mole ratio of creatinine to creatine against pH for solutions stable after 6 weeks incubation at 2° C., 22° C. and 39° C. (as described in Example 5)

The final mole:mole creatinine to creatine ratios of the solutions prepared with the same initial pH's were not identical in the three sets of incubations. However, as shown in FIG. 7, the mole:mole creatinine to creatine ratios for the 3 temperatures were very close to each other when these were compared with the final pH of each solution. Thus the mole:mole ratio at equilibrium of solutions of creatine and creatinine of different pH, are primarily influenced by pH and not by temperature.

Figure 8:
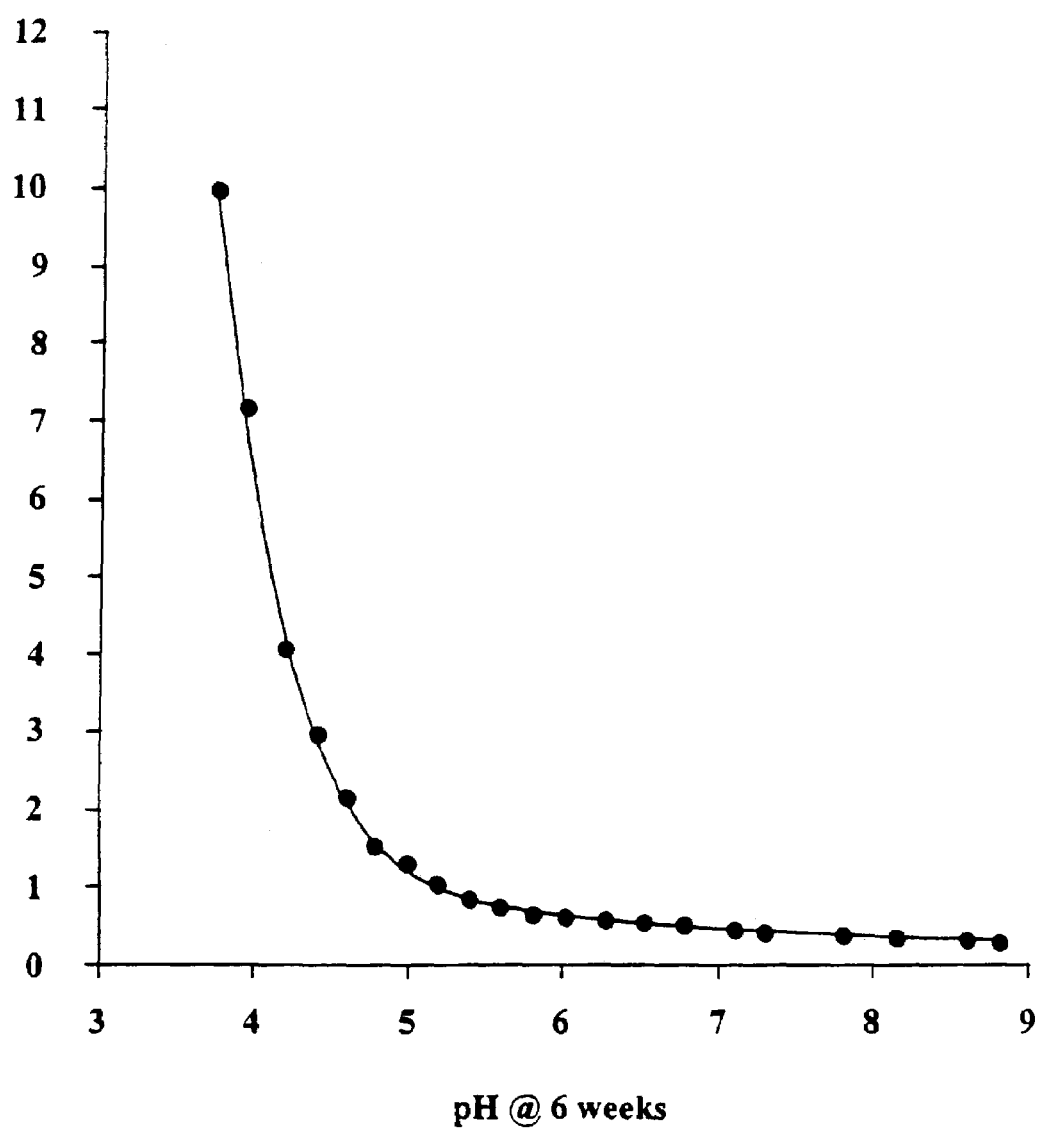
FIG. 8 is a graph of the mole:mole ratio of creatinine to creatine against pH for solutions stable after 6 weeks incubation at 22° C. (as described in Example 5), also shown is a 7th order polynomial line of best fit.

FIG. 8 shows the mole:mole creatinine to creatine ratios of the solutions at the different pHs at the end of 6 weeks incubation at 22° C. together with the 7th order polynomial line which bests this data (regression coefficient, r=1.00). The ratios predicted by this line are identical to those shown in FIG. 3 obtained after 17.7 weeks incubation at 22° C., but where the solutions were initially composed only of creatine and no creatinine. This confirms the data in the present example.

Discussion and Conclusions

Starting with solutions composed of creatine to creatinine in mole:mole ratios close to those in FIG. 3 to be those at equilibrium, stability was reached within 6 weeks when incubated between 2 and 39° C., and before 5 weeks when incubated at 39° C. Most probably equilibrium was reached much earlier at all three temperatures. The results shown in FIGS. 6 to 8 relate to creatine and creatinine when in stable equilibrium with each other and may be used to construct mole:mole ratios of creatinine to creatine at any pH from 3.8 to 8.8 which when mixed would immediately be at stable equilibrium.

At room temperature (22° C.) at a final pH of 4.6, the ratio of creatinine to creatine was 2.1:1. This is the upper limit considered as being practical for a stable drink containing creatine. Below a final pH of 4.6, the amount of creatinine to maintain the stability of creatine is excessive wasteful of material and impractical. At a final pH of 5.2 the ratio is about 1.0:1 which is a practical level and provides a palatable drink with an acidic pH. Compositions with pHs where the ratio is less than 1.0:1 are also practical and have the advantage of economy of materials, but have the disadvantage of not being so acidic and less palatable.

With refrigeration (e.g. 2° C.) the compositions recommended as useful for drinks are similar as those described above for room temperature. At 39° C. (considered to be the extreme of a high ambient temperature) the lowest pH supporting a mole:mole ratio of creatinine to creatine of 1.0:1 is 5.2–5.5 and defines the lowest pH for the practical range of compositions for drinks.

The most important factor influencing the ratio of creatine to creatinine at equilibrium is pH. If creatine and creatinine are mixed in the proportions at which they occur at equilibrium at a specified pH then these compositions will be immediately stable, as will also be the pH. When the initial composition is either side of that at equilibrium then concentrations of each will move towards those at equilibrium. If this involves formation of creatinine then the pH of the composition will increase, whereas if this involves formation of creatine then pH will decrease. The extent to which pH is changed will depend upon the absolute change in creatine or creatinine which must occur to reach equilibrium and the buffering capacity of the media. The time taken to reach equilibrium will be determined by how far the initial mole:mole ratio differs from that at equilibrium.

Warming or cooling produce an immediate effect on pH which if not reversed will drive the creatine/creatinine interconversion to a new equilibrium state. If cooling (e.g. refrigeration to 2° C.) is applied to a solution already at equilibrium then the effect will be to increase the creatine content at the expense of creatinine. This will "pull back" to some extent the initial (immediate) increase in pH with cooling before settling at a value still above the initial, supporting a lower mole:mole creatinine to creatine ratio. The time taken to reach a new equilibrium will be greatest at low pHs. With warming the opposite will happen with an initial decrease in pH which, if the compositions of creatine and creatinine were initially at equilibrium, will be "pulled back" to some degree towards the initial pH. Eventually the pH will settle at a pH lower than that before warming, and the composition will have a higher mole:mole creatinine to creatine ratio. Decreasing the pH by increasing the temperature will always cause a greater change in the mole:mole creatinine to creatine ratio than increasing the pH (by the same magnitude) by decreasing temperature. However, attainment of equilibrium will generally still be fastest when solutions are warmed rather than cooled. For solutions of low pH the time to attain a new equilibrium may be quite long.

Where compositions are prepared in which the concentrations of creatine and creatinine are significantly removed from those at equilibrium, and, where these solutions are then warmed or cooled for prolonged periods, then both factors described above will apply. In all of these cases, however, the extent of change may be minimized if the immediate influence on pH of warming or cooling of the base solution (i.e. the solution in the absence of added creatine and creatinine) is known and by applying the mole:mole creatinine to creatine ratios described in FIGS. 6 to 8 when preparing the composition.

Based on the data obtained above, Table 3 shows the creatinine to creatine mole:mole ratios of solutions of different pH at equilibrium and the corresponding concentrations of creatine (calculated as the monohydrate) and creatinine in a 500 ml drink. For convenience the concentration of creatine itself has been fixed in all cases to 5 g creatine monohydrate, and the concentration of creatinine allowed to vary accordingly.

TABLE 3

Estimated creatine and creatinine contents of a 500 ml drink of different pH's stored at 22° C. for 6 or more weeks.

| pH | mole Cn/mole Cr | Creatine monohydrate g/500 ml | Creatinine g/500 ml |
|---|---|---|---|
| 4.0 | 6.20:1 | 5 | 23.5 |
| 4.25 | 3.80:1 | 5 | 14.4 |
| 4.5 | 2.46:1 | 5 | 9.3 |
| 4.75 | 1.68:1 | 5 | 6.4 |
| 5.0 | 1.20:1 | 5 | 4.6 |
| 5.25 | 0.95:1 | 5 | 3.6 |
| 5.5 | 0.80:1 | 5 | 3.0 |
| 5.75 | 0.72:1 | 5 | 2.7 |
| 6.0 | 0.64:1 | 5 | 2.4 |
| 6.25 | 0.59:1 | 5 | 2.2 |
| 6.5 | 0.54:1 | 5 | 2.1 |
| 6.75 | 0.50:1 | 5 | 1.9 |
| 7.0 | 0.48:1 | 5 | 1.8 |
| 7.25 | 0.46:1 | 5 | 1.7 |

EXAMPLE 6

The preceding examples demonstrate the possibility of formulating a liquid composition comprising both creatine and creatinine, whereby the creatinine content of the composition renders the creatine content stable.

This example describes the detailed formulation of a carbonated energy drink (pH 4.4) in accordance with the invention comprising stable creatine (at 0.8 g/100 ml), creatinine, and a methyl xanthine stimulant.

| Contents | wt/litre |
|---|---|
| Creatine monohydrate | 8.0 g |
| Creatinine | 19.9 g |
| Glucose | 112 g |
| Citric acid monohydrate | 2.6 g |
| Sodium citrate dihydrate | 3.71 g |
| Taurine | 4.0 g |
| Glucuronolactone | 2.4 g |
| Caffeine | 300 mg |
| Niacin | 80 mg |
| Pantothenic acid | 20 mg |
| Vitamin B6 | 20 mg |
| Vitamin B12 | 20 mg |
| Add carbonated water to make a total volume of 1 liter | |

The above drink has a pH of 4.4 and is canned or bottled in volumes of 250 ml providing 2 g stable creatine monohydrate at room temperature. It is best served chilled.

EXAMPLE 7

A non-carbonated energy drink composition at pH 6.7 containing caffeine and 0.8 g/100 ml stable creatine The composition will be the same as in Example 6 except for the following changes

| Contents | wt/liter |
|---|---|
| Creatinine | 3.0 g |
| Citric acid monohydrate | 1.31 g |
| Sodium citrate dihydrate | nil |

| Contents | wt/liter |
|---|---|
| Di sodium hydrogen phosphate dihydrate | 6.68 g |
| Still mineral water is added to make a final volume of 1 litre. | |

The above drink has a pH of 6.7 and may be packaged in 250 ml cans suitably sterilized, providing 2 g stable creatine at room temperature. It is best served chilled.

EXAMPLE 8

A selection of beverages such as green and black tea with or without milk, lemon tea, drinking chocolate, filter and instant coffee were made up according to the supplier's instructions and the pH measured at room temperature as shown in Table 4. The quantity of creatinine required to achieve stability of 1.2 g creatine/100 ml at room temperature was then calculated using the molar ratios of creatinine to creatine at 22° C. obtained previously in Example 5, Table 1. Where appropriate the drinks may be consumed hot according to taste.

TABLE 4

The mole ratios and amounts of creatine and creatinine required to provide 1.2 g/100 ml stable creatine in different beverages containing caffeine

| | Beverage | Caffeine content mg/6 oz cup | pH | Mole:mole creatinine: creatine ratio (Cn/Cr) | Example: at infinite time | |
|---|---|---|---|---|---|---|
| | | | | | Creatine monohydrate content/100 ml | Creatinine content/100 ml |
| 1 | Jacksons Green Tea from Sainsburys | 15 | 6.89 | 0.485 | 1.20 g | 0.441 g |
| 2 | Black Tea (Aschcumb - Br Tea & Coffee Consortium) with milk | 50 | 6.86 | 0.49 | 1.20 g | 0.446 g |
| 3 | Cadburys drinking chocolate* | 10 | 6.76 | 0.50 | 1.20 g | 0.455 g |
| 4 | Black Tea (Aschcumb - Br Tea & Coffee Consortium) | 50 | 6.70 | 0.51 | 1.20 g | 0.464 g |
| 5 | Sainsburys individual coffee filters + milk | 150 | 5.95 | 0.64 | 1.20 g | 0.582 g |
| 6 | Edgecumbe instant coffee | 90 | 5.91 | 0.65 | 1.20 g | 0.591 g |
| 7 | Sainsburys individual coffee filters | 150 | 5.37 | 0.855 | 1.20 g | 0.886 g |
| 8 | Lift instant lemon tea | 30 | 4.27 | 3.73 | 1.20 g | 3.39 g |

*Cadbury's drinking chocolate also contains significant quantities of theobromine

What is claimed is:

1. A composition for human consumption, comprising creatine and a quantity of creatinine sufficient to render the creatine therein substantially stable when presented in an aqueous medium, and a methyl xanthine.

2. A composition according to claim 1, in which the mole:mole ratio of creatinine to creatine is not less than 1:10 and not more than 10:1.

3. A composition according to claim 2, in which the mole:mole ratio of creatinine to creatine is not less than 1:8 and not more than 5:1.

4. A composition according to claim 1, having a pH in the range 2.5 to 8.5.

5. A composition according to claim 4, having a pH in the range 3.0 to 7.0.

6. A composition according to claim 4, having a pH in the range 4.0 to 6.5.

7. A composition according to claim 4, having a pH in the range 4.5–5.5.

8. A composition according to claim 1, comprising one or more additional components selected from the group consisting of: vitamins, lipids, proteins, carbohydrates, polyols, amino acids, trace elements, colorings, flavors, artificial sweeteners, natural health and performance improving substances, antioxidants, stabilizers, preservatives and buffers.

9. A composition according to claim 1, in which the methyl xanthine comprises caffeine, theobromine, or a combination thereof.

10. A composition according to claim 1, comprising a methyl xanthine-containing extract obtained from one or more of the following: tea leaves; coffee beans; and cocoa pods.

11. A composition according to claim 1, comprising creatine suspended in an edible supporting matrix.

12. A composition according to claim 11, wherein the edible supporting matrix is selected from a group consisting of: honey, syrup, molasses, treacle, glycerol, Aloe Vera gel, plant derived polysaccharides, galactomannans, dextrans, guar gum, locust bean gum and xanthan gum.

13. A composition according to claim 1, presented as an aqueous solution.

14. A composition according to claim 1, in which the composition is a drink suitable for human consumption.

15. A composition according to claim 1, comprising a creatine concentration of at least 0.15 g/100 ml.

16. A composition according to claim 15, comprising a creatine concentration of at least 0.3 g/100 ml.

17. A composition according to claim 15, comprising a creatine concentration of at least 0.4 g/100 ml.

18. A composition according to claim 15, comprising a creatine concentration of at least 0.5 g/100 ml.

19. A composition according to claim 14, having a dose of methyl xanthine in the range 10 mg–1000 mg per drink.

20. A composition according to claim 1, further comprising taurine.

21. A drink composition according to claim 20, comprising a dose of taurine in the range 25–1000 mg per drink.

22. A composition according to claim 1, which is solid and which can be made into a drink by the addition of water.

23. A composition according to claim 1, wherein creatine is present in the form of creatine monohydrate or creatine phosphate.

24. A composition according to claim 1, wherein a normal serving thereof provides a physiologically effective dose of creatine.

25. A composition according to claim 1, wherein the creatine is substantially stable at a temperature of at least 25° C. for at least 7 days.

26. A composition according to claim 25, wherein the creatine is substantially stable at a temperature of at least 25° C. for at least 30 days.

27. A composition according to claim 25, wherein the creatine is substantially stable at a temperature of at least 25° C. for at least 60 days.

28. A composition according to claim 25, wherein the creatine is substantially stable at a temperature of at least 25° C. for at least 90 days.

29. A composition according to claim 25, wherein the creatine is substantially stable at a temperature of at least 25° C. for at least 120 days.

30. A composition according to claim 25, wherein the creatine is substantially stable at a temperature of at least 40° C. for at least 30 days.

31. A method of preparing a creatine containing composition for human consumption in which the creatine is substantially stable, the method comprising the steps of: providing, in the same composition, creatine and sufficient creatinine to render the creatine sufficiently stable when the composition is mixed with an aqueous medium and an amount of methyl xanthine.

32. A method according to claim 31, comprising the step of mixing an aqueous medium with creatine and creatinine.

33. A method according to claim 32, comprising the steps of:
providing a solution of creatine; subjecting the solution of creatine to suitable conditions so as at least partially to convert the creatine to creatinine, thereby forming sufficient creatinine to render the creatine in the resulting composition substantially stable, and adding an amount of methyl xanthine.

34. A method according to claim 33, wherein the step of subjecting the solution of creatine to suitable conditions involves heating the solution above ambient temperature.

35. A method according to claim 34, wherein the solution of creatine is heated to at least 90° C. for at least 30 minutes.

36. A method according to claim 32, comprising the steps of:
providing a solution of creatine; providing a solution of creatinine; and mixing the solutions so as to form a resulting composition in which there is sufficient creatine to render the creatine substantially stable, and adding an amount of methyl xanthine.

37. A method according to claim 36, wherein the pH of the solution of creatinine is lower than the pH of the solution of the resulting composition comprising creatine.

38. A method according to claim 36, wherein the pH of the solution of creatine is in the range 2.5 to 3.5, and the pH of the solution of the resulting composition comprising creatine is in the range 4.0 to 6.5.

39. A method according to claim 31, comprising the steps of:
providing solid creatine; providing solid creatinine; mixing the two solids so as to provide a resulting composition which, when dissolved in aqueous solution, provides a composition in which there is sufficient creatinine to render the creatine substantially stable, and adding an amount of methyl xanthine.

40. A method according to claim 31, further comprising the step of adding an edible supporting matrix.

41. A method according to claim 31, in which the resulting composition is acidic.

* * * * *